United States Patent [19]
Lynch et al.

[11] Patent Number: 5,919,937
[45] Date of Patent: Jul. 6, 1999

[54] PROCESS FOR PHOSPHODIESTERASE IV INHIBITORS

[75] Inventors: Joseph E. Lynch, Plainfield; Kenneth M. Wells, Neshanic Station; Yao-Jun Shi, Edison, all of N.J.

[73] Assignee: Merck & Co., Inc., Rahway, N.J.

[21] Appl. No.: 09/167,462

[22] Filed: Oct. 7, 1998

Related U.S. Application Data

[60] Provisional application No. 60/063,364, Oct. 29, 1997.

[51] Int. Cl.⁶ .................................................. C07D 213/30
[52] U.S. Cl. .......................... 546/340; 546/339; 546/344
[58] Field of Search .................................... 546/339, 340, 546/344

[56] References Cited

U.S. PATENT DOCUMENTS 5,808,082   9/1998   Choi et al. ............................... 546/334

*Primary Examiner*—Patricia L. Morris
*Attorney, Agent, or Firm*—J. Antonio Garcia-Rivas; Valerie J. Camara; Mark R. Daniel

[57] ABSTRACT

The invention encompasses a novel process for the formation of enantiomerically enriched mixtures of compounds of Formula I, which are useful precursors in the synthesis of phosphodiestersae IV inhibitors.

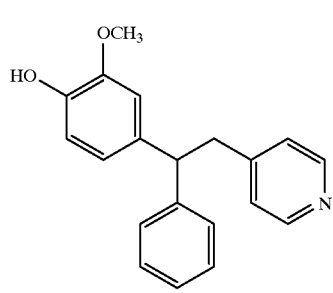

7 Claims, No Drawings

PROCESS FOR PHOSPHODIESTERASE IV INHIBITORS

This application claims the benefit of U.S. Provisional Application Ser. No. 60/063,364, filed Oct. 29, 1997.

BACKGROUND OF THE INVENTION

This invention relates to a process of making compounds for the treatment of diseases by raising the level of cyclic adenosine-3',5'-monophosphate (cAMP) through the inhibition of phosphodiesterase IV (PDE IV).

Many hormones and neurotransmitters modulate tissue function by elevating intra-cellular levels of adenosine 3', 5'-cyclic monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, seven members of the family have been described (PDE I–VII) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155 and Nicholson et al (1991) TIPS, 12: 19–27].

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P.T. et al., (1992) *J. Immunol.* 148 2503–2510) and eosinophils (Dent G. et al., (1991) *Br. J. Pharmacol.* 103 1339–1346) and that inhibition of this isotype is associated with the inhibition of cell activation. Furthermore, elevation of cAMP in airway smooth muscle has a spasmolytic effect. Consequently PDE IV inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. For PDE IV, it is has been shown that there are four isoforms (A, B, C and D) each coded for by a separate gene in both rodents (Swinnen J. V. et al., (1989) *Proc. Natl. Acad. Sci. USA* 86 5325–5329) and man (Bolger G. et al., (1993) *Mol. Cell Biol.* 13 6558–6571).

The existence of multiple PDE IVs raises the prospect of obtaining inhibitors that are selective for individual isoforms, thus increasing the specificity of action of such inhibitors. This assumes that the different PDE IV isoforms are functionally distinct. Indirect evidence in support of this comes from the selective distribution of these isoforms in different tissues (Swinnen et al., 1989; Bolger et al., 1993; Obernolte R. et al., (1993) *Gene* 129 239–247, ibid) and the high degree of sequence conservation amongst isoforms of different species.

To date full length cDNAs for human PDE IVA, B and D (Bolger et al., 1993 ibid; Obernolte et al., 1993 ibid; Mclaughlin M. et al., (1993) *J. Biol. Chem.* 268 6470–6476) and rat PDE IVA, B and D (Davis R. et al., (1989) *Proc. Natl. Acad. Sci. USA* 86 3604–3608; Swinnen J. V. et al., (1991) *J. Biol. Chem.* 266 18370–18377), have been reported, enabling functional recombinant enzymes to be produced by expression of the cDNAs in an appropriate host cell. These cDNAs have been isolated by conventional hybridisation methods. However using this approach, only partial cDNAs for both human and rat PDE IVC have been obtained. (Bolger et al., ibid. 1993 and Swinnen et al., ibid. 1989 and International Patent Specification No. WO 91/16457.)

The design of PDE IV inhibitors for the treatment of inflammatory diseases such as asthma, has met with limited success to date. Many of the PDE IV inhibitors which have been synthesised have lacked potency and/or inhibit more than one type of PDE isoenzyme in a non-selective manner. PDE IV inhibitors that are relatively potent and selective for PDE IV, are reported to be emetic as well. Indeed this side effect has been so universal that experts have expressed their belief that the emesis experienced upon administration of a PDE IV inhibitor, may be mechanism based.

We had previously reported a novel series of tri-substituted phenyl derivatives (Formula III), members of which, when compared to known structurally similar compounds, are potent inhibitors of PDE IV and have little or no inhibitory action on other PDE isoenzymes.

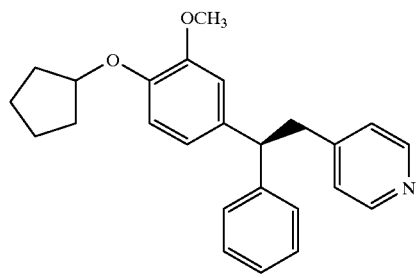

III

The preparation of these compounds is known in the literature. (See, e.g., WO 94/14742, published on Jul. 7, 1994; WO 95/17386, published on Jun. 29, 1995). However, the known syntheses of the enatiopure compounds involved the use of covalently bonded chiral auxilliaries, which lengthened the synthetic protocols and incresed the price and difficulty of preparation. We have discovered a short and efficient process to the enantiopure compounds using a resolution via crystallization.

SUMMARY OF THE INVENTION

The invention encompasses a process for the formation of enantiomerically enriched mixtures of compounds of Formula I, which are useful in the synthesis of phosphodiesterase IV inhibitor compounds, such as that represented by Formula III.

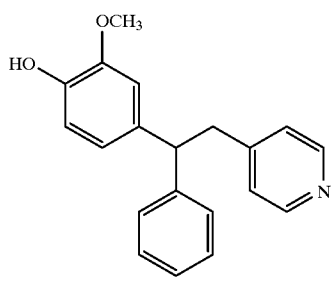

Also within the scope of the invention are salts of the compound of Formula I and (1S)-(+)-3-bromocamphor-10-sulfonic acid or (1)-(−)-3-bromocamphor-10-sulfonic acid.

DEFINITIONS:

| (Br—CSA) = | (1S)-(+)-3-bromocamphor-10-sulfonic acid or (1R)-(−)-3-bromocamphor-10-sulfonic acid |
|---|---|
| cAMP = | cyclic adenosine-3',5'-monophosphate |
| Cp = | cyclopentyl |
| DBU = | 1,8-diazabicyclo[5.4.0]undec-7-ene |
| DMF = | N,N-dimethylformamide |
| ee = | enantiomeric excess |
| LC = | liquid chromatography |
| LDA = | lithium diisopropylamide |
| NSAID = | non-steroidal anti-inflammatory drug |
| PDE = | phosphodiesterase |
| Ph = | phenyl |
| PY = | pyridyl |
| r.t. = | room temperature |
| rac. = | racemic |
| THF = | tetrahydrofuran |

DETAILED DESCRIPTION OF THE INVENTION

An embodiment of the present invention is a process for the production of an enantiomerically enriched mixture of a compound of Formula I

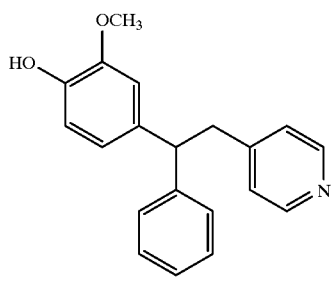

comprising, forming a salt of the compound of Formula I with (1S)-(+)-3-bromocamphor-10-sulfonic acid or (1R)-(−)-3-bromocamphor-10-sulfonic acid.

Another embodiment of the present invention is a process for the production of an enantiomerically enriched mixture of a compound of Formula I

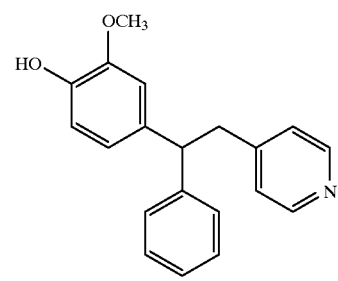

comprising,
a) mixing the compound of Formula I with (1S)-(+)-3-bromocamphor-10-sulfonic acid or (1R)-(−)-3-bromocamphor-10-sulfonic acid in an alcohol solvent system to form a mixture;
b) heating the mixture between about 60° C. and the reflux temperature of the alcohol solvent system;
c) allowing the mixture to cool so that a crystalline, bromocamphorsulfonic acid salt of compound I is formed;
d) filtering of the mixture to separate the crystalline salt from the supernatant; and
e) liberating compound I from the crystalline salt by treating the salt with a base.

A preferred embodiment is the process as recited above, wherein the alcohol solvent system is about 0.5% to about 5% water in an alcohol selected from the group consisting of: 1-propanol, 2-propanol, and 1-butanol.

A more preferred embodiment is wherein the bromocamphorsulfonic acid used in step (a) is (1S)-(+)-3-bromocamphor-10-sulfonic acid.

Another more preferred embodiment is wherein the alcohol solvent system consists of 1% water in n-propanol.

A most preferred embodiment wherein the alcohol solvent system in step (a) consists of 10% water in n-propanol and is heated to about 70° C. in step (b).

And another embodiment of the present invention is a crystalline salt of Formula II

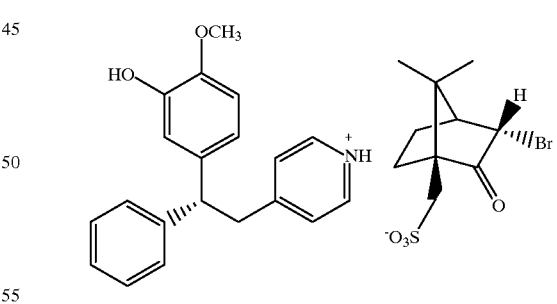

or the corresponding enantiomeric salt.

For purposes of this specification a compound is said to selectively inhibit PDE IV in preference to other PDE's if the ratio of the IC50 concentration for all other PDE inhibition to PDE IV inhibition is 100 or greater.

The term "enantiomerically enriched" as used in the application is intended to include compounds that are enantiomerically pure.

Utility:

The compounds according to the invention are useful intermediates in the preparation of phosphodiesterase inhibitors of Formula III. The PDE IV inhibitors of Fromula III are of particular use in the prophylaxis and treatment of human diseases where an unwanted inflammatory response or muscular spasm (for example bladder or alimentary smooth muscle spasm) is present and where the elevation of cAMP levels may be expected to prevent or alleviate the inflammation and relax muscle.

Particular uses for the compounds Formula III include the prophylaxis and treatment of asthma, especially inflamed lung associated with asthma, cystic fibrosis, or in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and artherosclerosis.

Compounds of Formula III also suppress neurogenic inflammation through elevation of cAMP in sensory neurones. They are, therefore, analgesic, anti-tussive and anti-hyperalgesic in inflammatory diseases associated with irritation and pain. Compounds according to the invention may also elevate cAMP in lymphocytes and thereby suppress unwanted lymphocyte activation in immune-based diseases such as rheumatoid arthritis, ankylosing spondylitis, transplant rejection and graft versus host disease.

Compounds of Formula III have also been found to reduce gastric acid secretion and therefore can be used to treat conditions associated with hypersecretion of gastric acid.

Compounds of Formula III suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators. They also suppress inflammation and pyrexia due to cytokines and are, therefore, useful in the treatment of inflammation and cytokine-mediated chronic tissue degeneration which occurs in diseases such as rheumatoid or osteoarthritis.

Over-production of cytokines such as TNF in bacterial, fungal or viral infections or in diseases such as cancer, leads to cachexia and muscle wasting. Compounds of the invention ameliorate these symptoms with a consequent enhancement of quality of life.

Compounds of Formula III also elevate cAMP in certain areas of the brain and thereby counteract depression and memory impairment.

They also suppress cell proliferation in certain tumour cells and can be used, therefore, to prevent tumour growth and invasion of normal tissues.

Synthesis of Compounds of Formula I

Racemic phenol 5 may be synthesized by the procedure disclosed in European Patent No. 626939, which is hereby incorporated by reference, or by the scheme shown below. (1S)-(+)-3-bromocamphor-10-sulfonic acid may be purchased as the hydrate from Aldrich (Milwaukee, Wis.). Althernatively, either isomer may be synthesized by the method described in *Beilstein* 11, 317.

Scheme 1

The Grignard reaction of isovanillin (2) with 2.0 equivalent of phenylmagnesium bromide at $-10°$ C. produced alcohol 3, which was isolated from. Alcohol 3 was then converted to chloride 4 using thionyl chloride in toluene at $0°$ C. The residue after evaporation was dissolved in THF and treated with the litho picolate (generated from LDA and picoline) at $-60°$ C. After work up and crystallization from isopropanol, compound 5 was obtained in racemic form.

Scheme 1

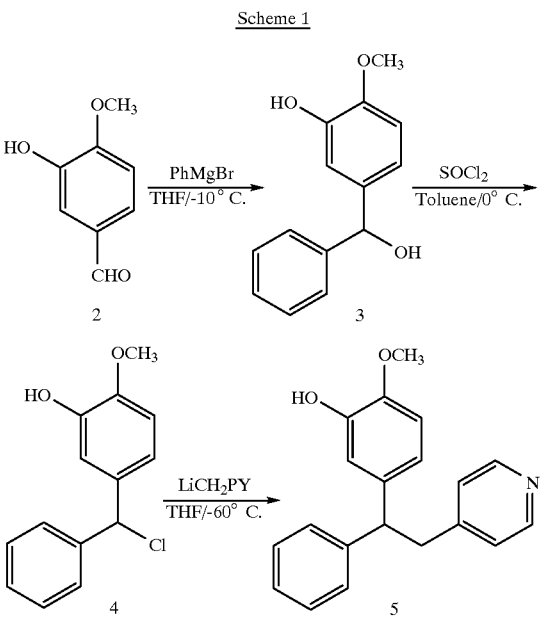

Scheme 2

The isolated racemic pyridine phenol 5, a highly crystalline solid, was treated with (1S)-(+)-3-bromocamphor-10-sulfonic acid (Br-CSA) (6) in aqueous n-propanol to provide the salt 7 which contained an 88% ee of the desired enantiomer (R)-7. Recrystallization of the isolated salt 7 from aqueous n-propanol afforded optically pure 7 (>99.5% ee). Thus, a highly efficient resolution of racemic pyridine phenol 5 was accomplished in good overall yield and >99.5% ee.

To complete the synthesis, the salt 7 was neutralized with 2N NaOH to afford the enantiopure phenol (R)-8. Subsequent cyclopentylation of (R)-8 was carried out with cyclopentyl bromide (CpBr) and cesium carbonate in DMF (no racemization was observed). The final product (1) was obtained as a bisulfate salt.

Scheme 2

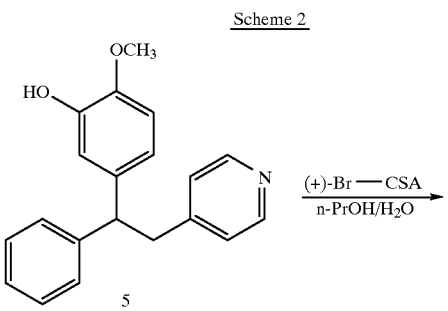

7
-continued

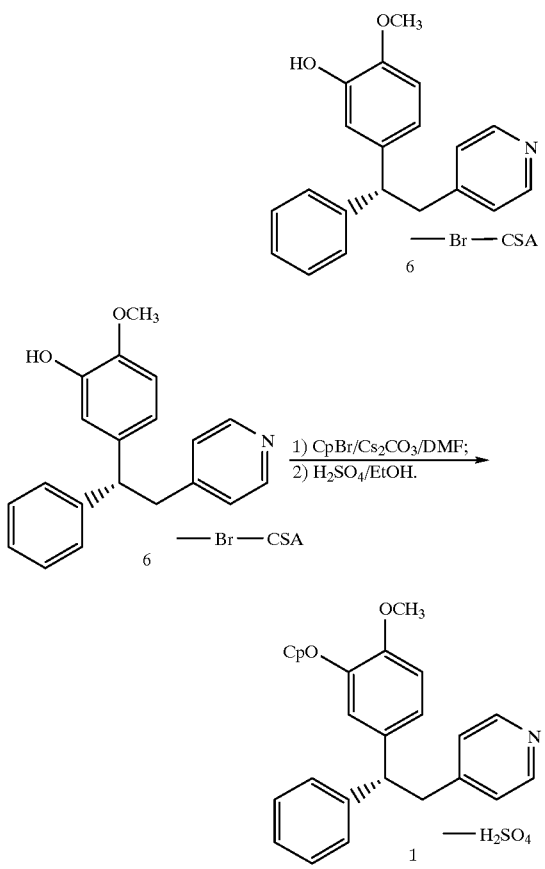

HPLC ASSAY METHODS

A. Determination of Purity:

The purity of the mentioned compounds was determined using an Rx C-8 column under the following conditions:

Flow rate=1.0 mL/min;
λ=210 nm;
Mobile phase: A=acetonitrile; B=$H_2O$/0.1% $H_3PO_4$;
Gradient Utilized:

| Time (min.) | % A | % B |
|---|---|---|
| 0 | 30 | 70 |
| 25 | 70 | 30 |
| 26 | 30 | 70 |
| 30 | 30 | 70 |

Retention Times:

Phenol 5: 6.0 minutes

Compound 1: 12.9 minutes

B. Determination of Enantiomeric Excess

Enantiomeric excess was determined using a CHIRAL-CEL OJ column (available from Chiral Technologies, Inc. in Exton, Pa.) under the following conditions:

Flow rate=1.0 mL/min;
λ=210 nm;
Mobile phase 30% EtOH/Hexane
Retention Times:

(S)-enantiomer 1: 17.4 minutes (R)-enantiomer 1: 19.8 minutes

8

EXAMPLE 1

Resolution of Phenol 5

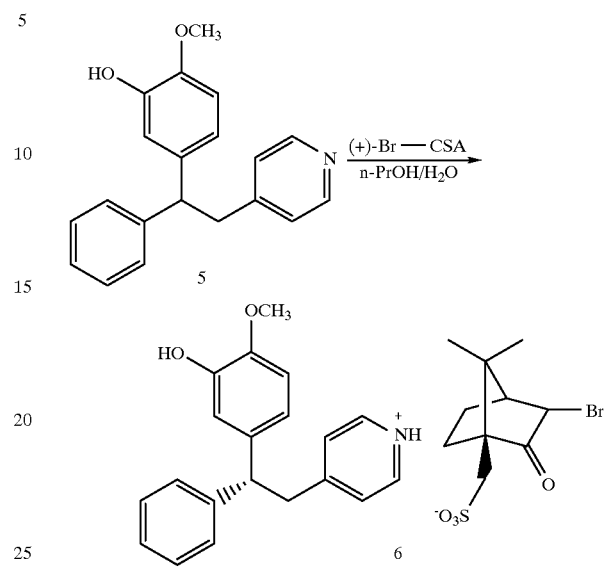

To a 125 ml round bottom flask with magnetic bar and $N_2$ inlet containing 37.5 mL of 1-propanol and 375 μL of water was added 1.73 g (5.75 mmol) of racemic phenol 1. 1.87 g (5.69 mmol) of (1S)-(+)-3-bromocamphor-10-sulfonic acid was then added and the slurry was heated to 70° C. All solids dissolved. The solution was cooled to 58° C. and seeded. The resulting thin slurry was aged at 55° C. for one hour and then cooled to room temperature over one hour. The white slurry was aged for one hour at room temperature and subsequently filtered through a glass funnel. The crystals were washed with 2 ml n-propanol and dried at 45° C. overnight in a vacuum oven. The recovered crystalline salt had an enantiomeric excess of 88% as determined by chiral LC of the free base under the conditions mentioned above.

EXAMPLE 2

Recrystallization of the Acid-base Pair 6

To a 125 ml round bottom flask with magnetic bar and $N_2$ inlet containing 4.0 mL of 1-propanol and 400 μL of water was added 413 mg of salt 7. The white slurry was heated to 70° C. until all the solids had dissolved. The reaction mixture was then cooled to 55° C. and seeded. The thin slurry for then aged for one hour at 52° C., cooled to room temperature over one hour and aged for an additional hour. The crystals were then filtered through a glass funnel and washed with 1 ml n-propanol. The recovered salt 6 had an enantiomeric excess of over 99.5% as determined by the chiral LC method described above. m.p. 185–187° C.

EXAMPLE 3

Cyclopentylation of the Phenolic Moiety to Yield PDE 1

To a 125 ml round bottom flask with magnetic stir bar was added 1.02 g (1.61 mmol) of salt 6 and 25 mL ethyl acetate. To this slurry was added 15 mL $H_2O$ and the pH was adjusted to 4.5 with 2N NaOH (about 1 mL). The organic phase was then washed with 20 mL $H_2O$ and dried with magnesium sulfate. The solution was filtered and evaporated to an oil. The residue was dissolved in 4.0 mL DMF and placed in a 15 mL round bottom flask with a magnetic stir bar and $N_2$ inlet. 1.07 g (3.3 mmol) of cesium carbonate and 354 μL (3.3 mmol) of cyclopentylbromide were then added and the thin white slurry was stirred overnight at room temperature. The reaction was monitored by LC using the purity assay disclosed above. When the starting material was reduced to >0.1% (approximately 16–18 hours), the reaction was quenched with 10 mL $H_2O$. The quenched solution was extracted twice with ethyl acetate (about 20 mL total ) and the combined organics were wash with 20 mL $H_2O$. The organic layer was removed under reduced pressure and the crude residue was dissolved in 6.0 mL of ethyl alcohol. 90.0 mL (1.61 mmol) of sulfuric acid were then added and the sulfate salt precipitated from the solution. The slurry was aged one hour, filtered and washed with ethyl alcohol. After drying at 40° C. under vacuum overnight, compound 1 was obtained as a bright white crystals.

What is claimed is:

1. A process for the production of an enantiomerically enriched mixture of a compound of Formula I

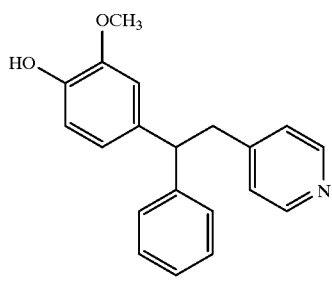

comprising, forming a salt of the compound of Formula I with (1S)-(+)-3-bromocamphor-10-sulfonic acid or (1R)-(−)-3-bromocamphor-10-sulfonic acid.

2. A process for the production of an enantiomerically enriched mixture of a compound of Formula I

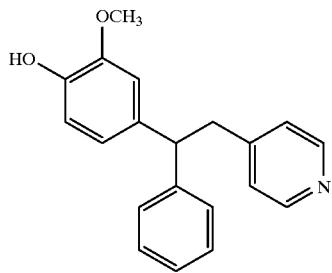

comprising, a) mixing the compound of Formula I with (1S)-(+)-3-bromocamphor-10-sulfonic acid or (1R)-(−)-3-bromocamphor-10-sulfonic acid in an alcohol solvent system to form a mixture;

b) heating the mixture between about 60° C. and the reflux temperature of the alcohol solvent system;

c) allowing the mixture to cool so that a crystalline, bromocamphorsulfonic acid salt of compound I is formed;

d) filtering of the mixture to separate the crystalline salt from the supernatant; and e) liberating compound I from the crystalline salt by treating the salt with a base.

3. The process as recited in claim 2, wherein the alcohol solvent system is about 0.5 to about 5% water in an alcohol selected from the group consisting of: 1-propanol, 2-propanol, and 1-butanol.

4. The process as recited in claim 2, wherein the bromocamphorsulfonic acid used in step (a) is (1S)-(+)-3-bromocamphor-10-sulfonic acid.

5. The process as recited in claim 2, wherein the alcohol solvent system consists of 1% water in n-propanol.

6. The process as recited in claim 5, wherein the alcohol solvent system is heated to about 70° C. in step (b).

7. A crystalline salt of Formula II

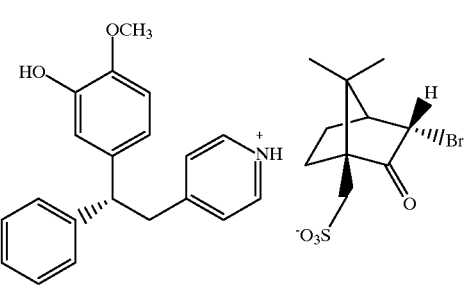

or the corresponding enantiomeric salt.

* * * * *